(12) United States Patent
Pongpeerapat

(10) Patent No.: US 10,675,254 B2
(45) Date of Patent: Jun. 9, 2020

(54) SPHINGOSINE-1-PHOSPHATE RECEPTOR AGONIST IONTOPHORETIC DEVICES AND METHODS OF USING THE SAME

(71) Applicant: Teikoku Seiyaku Co., Ltd., Higashikagawa, Kagawa (JP)

(72) Inventor: Adchara Pongpeerapat, San Jose, CA (US)

(73) Assignee: Teikoku Seiyaku Co., Ltd., Higashikagawa, Kagawa (JP)

( * ) Notice: Subject to any disclaimer, the term of this patent is extended or adjusted under 35 U.S.C. 154(b) by 835 days.

(21) Appl. No.: 14/473,598

(22) Filed: Aug. 29, 2014

(65) Prior Publication Data

US 2015/0105712 A1 Apr. 16, 2015

Related U.S. Application Data

(60) Provisional application No. 61/889,951, filed on Oct. 11, 2013.

(51) Int. Cl.
*A61K 31/137* (2006.01)
*A61K 9/00* (2006.01)
*A61N 1/30* (2006.01)

(52) U.S. Cl.
CPC .......... *A61K 31/137* (2013.01); *A61K 9/0009* (2013.01); *A61N 1/30* (2013.01)

(58) Field of Classification Search
CPC ... A61N 1/0448; A61K 31/137; A61K 9/0009
USPC .................................................. 604/20, 501
See application file for complete search history.

(56) References Cited

U.S. PATENT DOCUMENTS

| 4,578,061 | A | 3/1986 | Lemelson |
| 5,232,438 | A | 8/1993 | Theeuwes et al. |
| 5,505,715 | A | 4/1996 | Shah et al. |
| 5,604,229 | A | 2/1997 | Fujita et al. |
| 6,004,565 | A | 12/1999 | Chiba et al. |
| 6,121,329 | A | 9/2000 | Fujii et al. |
| 7,856,263 | B2 * | 12/2010 | Anderson ............ A61N 1/0428 424/449 |
| 7,905,852 | B2 | 3/2011 | Jennings-Spring |
| 2005/0090520 | A1 | 4/2005 | Lindquist |

(Continued)

FOREIGN PATENT DOCUMENTS

| TW | 201014564 A | 4/2010 |
| WO | WO20100055027 A3 | 5/2010 |

OTHER PUBLICATIONS

Kappos et al., A Placebo-Controlled Trial of Oral Fingolimod in Relapsing Multiple Sclerosis, the New England Journal of Medicine (2010), 362(5):387-401.

(Continued)

*Primary Examiner* — Phillip A Gray
(74) *Attorney, Agent, or Firm* — Khin K. Chin; Bret E. Field; Bozicevic, Field & Francis LLP

(57) ABSTRACT

Iontophoretic devices for transdermal delivery of a sphingosine-1-phosphate receptor agonist active agent are provided. Also provided are methods of transdermally delivering a therapeutically effective amount of a sphingosine-1-phosphate receptor agonist active agent to a subject, e.g., to treat immune system disorders such as multiple sclerosis. Packaged iontophoretic systems, kits including iontophoretic devices, and methods of making iontophoretic devices are also provided.

17 Claims, 3 Drawing Sheets

(56) References Cited

U.S. PATENT DOCUMENTS

| | | | |
|---|---|---|---|
| 2007/0083186 A1* | 4/2007 | Carter | A61N 1/30 |
| | | | 604/501 |
| 2008/0058703 A1 | 3/2008 | Subramony et al. | |
| 2009/0005722 A1 | 1/2009 | Jennings-Spring | |
| 2009/0275553 A1 | 11/2009 | Kovarik et al. | |
| 2010/0160259 A1 | 6/2010 | Schmouder et al. | |
| 2010/0168078 A1 | 7/2010 | Hiestand et al. | |
| 2012/0141513 A1* | 6/2012 | Liu | C07C 215/28 |
| | | | 424/184.1 |

OTHER PUBLICATIONS

Cohen et al., Oral Fingolimod or Intramuscular Interferon for Relapsing Multiple Sclerosis, the New England Journal of Medicine (2010), 362(5):402-415.

Mitsubishi UFJ Securities, Unment medical needs key, Japan Equity Research, Industry Update, Oct. 9, 2009, 19 pages.

* cited by examiner

FIG. 1A – Cumulative Drug Delivered
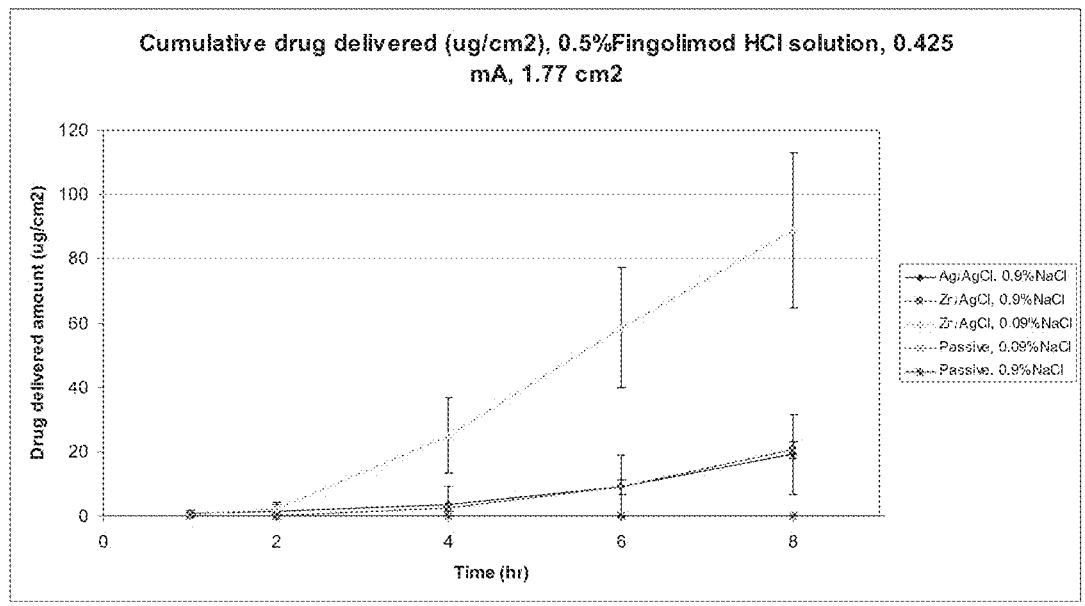
FIG. 1B – Drug Delivery Efficiency
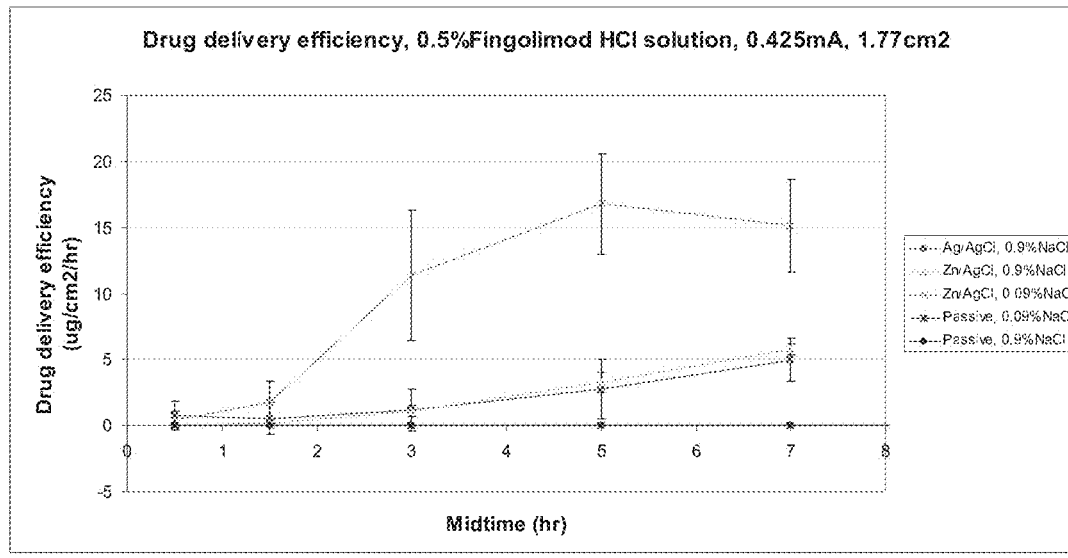

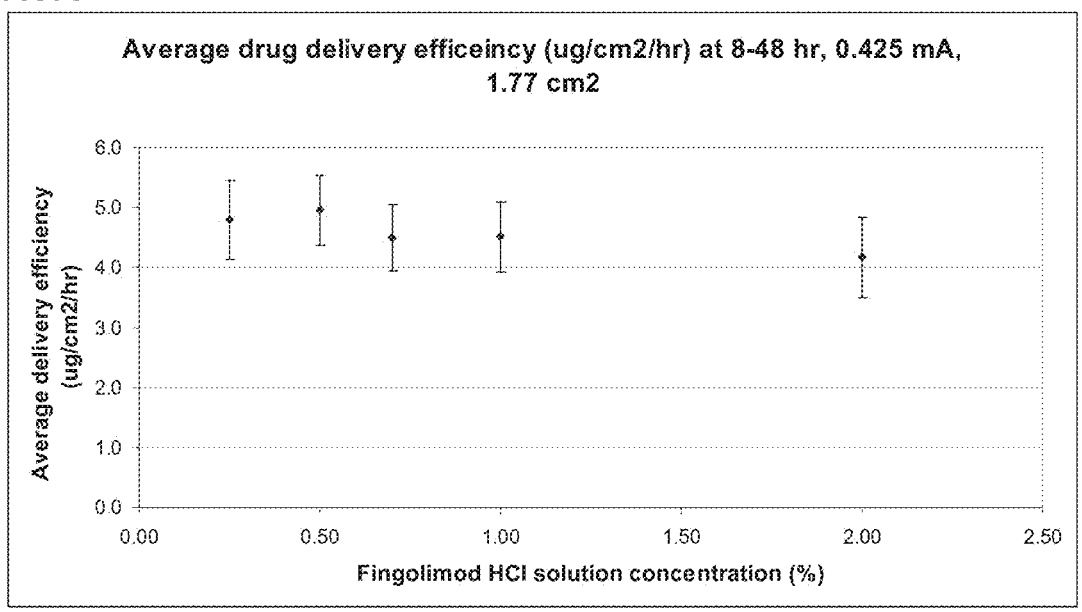

SPHINGOSINE-1-PHOSPHATE RECEPTOR AGONIST IONTOPHORETIC DEVICES AND METHODS OF USING THE SAME

CROSS-REFERENCE TO RELATED APPLICATIONS

Pursuant to 35 U.S.C. § 119(e), this application claims priority to the filing date of U.S. Provisional Application Ser. No. 61/889,951 filed Oct. 11, 2013, the disclosure of which is herein incorporated by reference.

INTRODUCTION

Nerve cells communicate by sending electrical signals, or action potentials, down long fibers called axons, which are wrapped in a fatty insulating substance called myelin. Multiple sclerosis (MS) is a disease in which the fatty myelin sheaths around the nerve axons of the brain and spinal cord are damaged, leading to demyelination and scarring of the axons. MS affects the ability of nerve cells in the brain and spinal cord to communicate with each other. In MS, the body's own immune system attacks and damages the myelin. When myelin is lost, the axons can no longer effectively conduct electrical signals.

Modulators of sphingosine-1-phosphate receptors have been developed for the treatment of inflammatory disorders and autoimmune conditions. For example, a 2-amino-1,3-propanediol compound designated fingolimod (a.k.a. FTY720) is a sphingosine-1-phosphate receptor agonist that has immunosuppressive activity. Fingolimod is derived from the myriocin (a.k.a. ISP-1) metabolite of the fungus *Isaria sinclairii*. Fingolimod is a structural analogue of sphingosine and is phosphorylated by sphingosine kinases in the cell. Fingolimod acts by sequestering lymphocytes in lymph nodes, preventing the lymphocytes from moving to other regions of the body, e.g., the central nervous system where they can play a role in autoimmune responses such as those underlying multiple sclerosis. It is believed that Fingolimod is effective for the treatment of MS due to its ability to sequester myelin antigen-specific CD4 T cells and IFN-gamma type 1 helper T cells into the lymph nodes, reducing the infiltration of these T cells into the CNS where they are free to damage the myelin sheaths around the nerve axons.

SUMMARY

Iontophoretic devices for transdermal delivery of a sphingosine-1-phosphate receptor agonist active agent are provided. Also provided are methods of transdermally delivering a therapeutically effective amount of a sphingosine-1-phosphate receptor agonist active agent to a subject, e.g., to treat immune system disorders such as multiple sclerosis. Packaged iontophoretic systems, kits including iontophoretic devices, and methods of making iontophoretic devices are also provided.

BRIEF DESCRIPTION OF THE DRAWINGS

FIGS. 1(A) & 1(B). In-vitro Fingolimod HCl delivery obtained from 0.5% Fingolimod HCl solution. (A) Cumulative drug delivered; (B) Drug delivery efficiency.

FIG. 3 In-vitro fingolimod HCl delivery as a function of drug concentration.

DETAILED DESCRIPTION

Figure 2A:
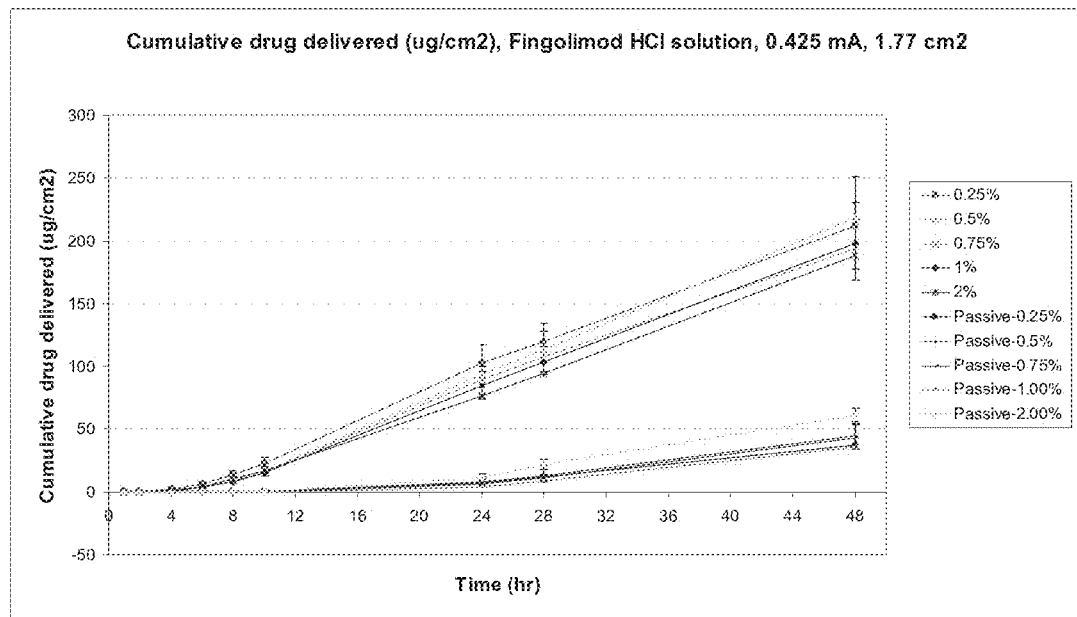
FIGS. 2(A) & 2(B). In-vitro Fingolimod HCl delivery obtained from 0.25, 0.5, 0.75, 1 and 2% fingolimod HCl solution. (A) Cumulative drug delivered; (B) Drug delivery efficiency.

Iontophoretic devices for transdermal delivery of a sphingosine-1-phosphate receptor agonist active agent are provided. Also provided are methods of transdermally delivering a therapeutically effective amount of a sphingosine-1-phosphate receptor agonist active agent to a subject, e.g., to treat immune system disorders such as multiple sclerosis. Packaged iontophoretic systems, kits including iontophoretic devices, and methods of making iontophoretic devices are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the invention, embodiments of the devices will be described first in greater detail. Thereafter, aspects of embodiments of the methods are described in greater detail. Next, aspects of embodiments of the packaged devices, kits, and methods of making electrophoretic devices are described in greater detail.

Devices

As summarized above, aspects of the invention include iontophoretic devices that include a sphingosine-1-phosphate receptor agonist active agent. Iontophoretic devices are devices configured to deliver an active agent through the skin in conjunction with an applied electric field. An "iontophoretic device", as used herein, refers to an electrically-assisted device or apparatus suitable for the transdermal iontophoretic delivery of an agent to a subject. The term "iontophoretic delivery" refers generally to the delivery of an active agent through the skin, wherein such delivery is induced or aided by the application of electric current, e.g., via the electrically induced transport of charged ions.

Any type of iontophoretic device may be used to transdermally deliver the sphingosine-1-phosphate receptor agonist active agent to a subject. For example, the invention provides "conventional" iontophoretic devices, such as those including two electrodes configured to be attached to a patient, each electrode connected via a wire to a microprocessor-controlled electrical instrument. In such conventional devices, the sphingosine-1-phosphate receptor agonist active agent is placed under one (e.g., an anode electrode) or both electrodes for delivery into the body as the instrument is activated. The instrument is configured to regulate current flow and application time. Power sources for such devices may include batteries (e.g., DC batteries), an electrical outlet, or any suitable power source, which when providing power for the microprocessor-controlled circuitry allow application of a voltage to the electrodes to create a regulated current flow.

In addition to conventional iontophoretic devices, the present invention provides iontophoretic devices for transdermal delivery of a sphingosine-1-phosphate receptor agonist active agent, which devices are configured to be worn on the skin of a subject (i.e., a "wearable" iontophoretic device). Wearable iontophoretic devices of the invention may be "integrated," meaning that each component, e.g., two or more electrodes, one or more power sources, etc. are part of a single self-contained unit (e.g., an iontophoretic patch) that is attached to a skin surface of the subject.

Wearable iontophoretic devices of the invention are generally of a size and weight that permits the subject to wear the device without significant (or little if any) impairment of the subject's mobility. For example, the subject may be able to walk and readily move the part of the body (e.g., an arm, a leg, torso, head, etc.) to which the wearable iontophoretic device is attached. According to one embodiment, wearable iontophoretic devices of the invention weigh from 0.1 g to 200 g, such as from 0.5 g to 100 g, e.g., from 1 g to 60 g. In certain aspects, wearable iontophoretic devices of the invention are sized to cover an area of a skin surface of a subject from 0.5 to 1000 $cm^2$, such as from 1 to 500 $cm^2$, e.g., from 2 to 100 $cm^2$.

The shape of the wearable iontophoretic device (e.g., an iontophoretic patch) may vary, where shapes of interest include, but are not limited to: square, rectangle, oval, circle, etc. The subject wearable iontophoretic devices may be packaged by means of a heat seal in a packaging material that includes a layer of aluminum to obtain the final product.

According to one embodiment, wearable iontophoretic devices of the invention are configured to be reusable, e.g., such that the power source is designed to be replaceable and/or the device may be resupplied with active agent for iontophoretic delivery of two or more doses of active agent. In other aspects, the wearable iontophoretic devices are disposable, in which the entire wearable iontophoretic system is designed to be disposed following a single use, consumption of the original power source and/or depletion of the active agent. For example, the iontophoretic device may be a Wearable Electronic Disposable Drug delivery technology (WEDD®) device, e.g., as described in U.S. Publication No. 2011/0245755, International Publication No. 2010/027468, and U.S. Pat. Nos. 7,856,263, 7,844,327, 7,031,769, 7,031,768, 6,745,071, 6,653,014 and 6,421,561, the disclosures of which are herein incorporated by reference in their entireties for all purposes.

Iontophoretic devices of the invention (e.g., conventional, wearable or any other type of iontophoretic device) may include a donor reservoir and a counter reservoir. By "donor reservoir" is meant a reservoir that includes (or is configured to include) the sphingosine-1-phosphate receptor agonist active agent for transdermal delivery to the subject. The donor reservoir may include one or more donor electrodes (e.g., 1, 2, or more donor electrodes). The counter reservoir may include a counter electrode which serves to close the electrical circuit through the body. In conjunction with the patient's skin contacted by the electrodes, the circuit is completed by a power source (e.g., a battery or non-battery based power source) electrically coupled to the donor reservoir and the counter reservoir (e.g., by electrically connecting a donor electrode associated with the donor reservoir and a counter electrode associated with the counter reservoir). If the sphingosine-1-phosphate receptor agonist active agent to be delivered into the body is positively charged, then the donor electrode may be an anode and the counter electrode may be a cathode that serves to complete the circuit. If the sphingosine-1-phosphate receptor agonist active agent to be delivered into the body is negatively charged, then the donor electrode may be a cathode and the counter electrode may be an anode that serves to complete the circuit. As will be appreciated, iontophoretic devices of the invention may include two donor reservoirs for simultaneous delivery of active agents of opposite charge across the skin of a subject.

In certain embodiments, the sphingosine-1-phosphate receptor agonist active agent is uncharged, and the subject iontophoretic devices are configured to transdermally deliver the uncharged active agent into the body of the subject by electroosmosis. By electroosmosis is meant the transdermal flux of a liquid solvent containing the active agent which is induced by the presence of an electric field established across the skin by the donor electrode.

Sphingosine-1-Phosphate Receptor Agonist Active Agents

Iontophoretic devices of the present disclosure are configured to transdermally deliver a sphingosine-1-phosphate receptor agonist active agent to a subject. As used herein, a "sphingosine-1-phosphate receptor agonist" may be any compound or composition of matter that binds to one or more of the sphingosine-1-phosphate receptors of a cell, and optionally triggers a response by that cell. For example, the sphingosine-1-phosphate receptor agonist may be a compound or composition of matter that binds to sphingosine-1-phosphate receptor 1 (S1P1), sphingosine-1-phosphate receptor 2 (S1P2), sphingosine-1-phosphate receptor 3 (S1P3), sphingosine-1-phosphate receptor 4 (S1P4), or sphingosine-1-phosphate receptor 5 (S1P5), or any combination thereof. By "active agent" is meant a compound or composition of matter which, when administered to an organism (human or animal) induces a desired pharmacologic and/or physiologic effect. The active agents herein are local sphingosine-1-phosphate receptor agonists and pharmacologically acceptable salts, bases, esters, amides, derivatives, polymorphs or prodrugs thereof.

In certain aspects, the sphingosine-1-phosphate receptor agonist active agent is a 2-amino-1,3-propanediol compound, derivative thereof and/or salt thereof. For example, the sphingosine-1-phosphate receptor agonist active agent may be a 2-amino-2-[2-(4-octylphenyl)ethyl]propane-1,3-diol compound (or salt thereof) that binds to one or more of S1P1-S1P5. In one aspect, the sphingosine-1-phosphate receptor agonist active agent is fingolimod or a salt thereof. Where the active agent is present as a salt, the salt may vary. In some instances, the salt is selected from chloride, bromide, maleate, fumarate, ascorbate, succinate, oxalate, phosphate, mandelate, adipate, ethanesulfonate, naphthalene-1,5-disulfonate, naphthalene-1-sulfonate, naphthalene-2-sulfonate, L-aspartate, 4-acetamidobenzoate, (+) camphorate, (+) camphor-10-sulfonate, decanoate, hexanoate, octanoate, cinnamate, dodecylsulfate, ethane-1,2-disulfonate, 2-hydroxyethanesulfonate, glutarate, DL-lactate, 1-hydroxy-2-naphthoate, laureate, salicylate, tartrate, mesylate, citrate, benzoate or mixtures thereof. Specific sphingosine-1-phosphate receptor agonist active agents of interest include, but are not limited to: fingolimod HCl, fingolimod HBr, fingolimod maleate and fingolimod fumarate. Also of interest are polymorphic forms of such agents, such as polymorphic forms of fingolimod hydrochloride The donor reservoir may comprise a donor medium, where the sphingosine-1-phosphate receptor agonist active agent (e.g., fingolimod HCl) is present in the donor medium. In some instances, the sphingosine-1-phosphate receptor agonist active agent is the only active agent in the donor medium. The donor medium may be a matrix material adapted to absorb and hold a sufficient quantity of liquid therein in order to permit transport of the agent therethrough by iontophoresis. In one aspect, the donor medium is a hydrophilic polymer matrix (e.g., an aqueous hydrogel, a suspension, a solution, etc.) in which the sphingosine-1-phosphate receptor agonist active agent is present. Both synthetic and natural hydrophilic polymer matrices that find use in iontophoretic devices and in which the active agent may be present are described elsewhere herein.

The sphingosine-1-phosphate receptor agonist active agent may be present in the donor medium in an amount sufficient to deliver a desired dose of the agonist to a subject. For example, the sphingosine-1-phosphate receptor agonist active agent (e.g., fingolimod HCl) may be present in the donor medium (e.g., a hydrogel) in an amount sufficient to iontophoretically deliver a dose of from 0.01 to 10 mg to a subject in a single day, such as from 0.05 to 5 mg in a single day, from 0.1 to 2 mg in a single day, e.g., 0.25 mg, 0.5 mg, 0.75 mg, 1.0 mg, 1.25 mg or 1.5 mg in a single day. According to one embodiment, the iontophoretic device is a wearable (and optionally disposable) iontophoretic device configured for delivery of the sphingosine-1-phosphate receptor agonist active agent over the course of from 1 hours to 7 days or more, e.g., 2, 3, 4, 5, 6, 8, 10, 12 hr and including 1, 2, 3, 4, 5, 6, or 7 or more days, during which the above dosages of the active agent (e.g., 0.25 mg, 0.5 mg, 0.75 mg, 1.0 mg, 1.25 mg, 1.5 mg, etc.) are delivered on a daily basis by a single iontophoretic device.

In certain aspects, the concentration of the sphingosine-1-phosphate receptor agonist active agent (e.g., fingolimod HCl) in the donor medium ranges from 0.0002 mg/ml to 20,000 mg/ml, such as from 0.0011 mg/ml to 10,000 mg/ml, for example, from 0.0022 mg/ml to 4,000 mg/ml.

Donor Reservoirs

Iontophoretic devices of the present disclosure include a donor reservoir that comprises a sphingosine-1-phosphate receptor agonist. The donor reservoir includes at least one donor electrode (e.g., anode) assembly. The donor reservoir is capable of ionic communication with the skin, such that the boundary between the donor reservoir and the skin is permeable to the sphingosine-1-phosphate receptor agonist (and optionally permeable to other ions), as the current is carried by ions traversing across the boundary. The donor reservoir is also in electrical communication with at least one donor electrode (e.g., two or more donor electrodes) of the iontophoretic device.

The donor reservoir is constructed to permit ionic communication with the skin and electrical communication with the electrode. The structure of the donor reservoir may vary depending upon the desired application and may include a liquid, semi-liquid, semi-solid, or solid material. The donor reservoir may be a hydrogel, suspension, or solution (e.g., with woven or non-woven material), as desired.

The donor reservoir may include a matrix material adapted to absorb and hold a sufficient quantity of liquid therein in order to permit transport of the agent therethrough by iontophoresis. In certain aspects, gauzes made of cotton or other absorbent fabrics as well as pads and sponges (both natural and synthetic) may be used. According to one embodiment, the donor reservoir includes a matrix composed, at least in part, of a hydrophilic polymer material (e.g., a hydrogel). Both natural and synthetic hydrophilic polymers may be used. Suitable hydrophilic polymers include, but are not limited to: polyvinylpyrrolidones, including polyvinylpyrrolidone copolymers, such as polyvinylpyrrolidone-vinyl acetate copolymer (PLASDONE® polymers manufactured by ISP); polyvinyl alcohol; polyalkene oxides, such as polyethylene oxides, including POLYOX® polymers manufactured by Union Carbide Corp., copolymers including block copolymers and grafted polymers such as poloxamers, e.g., PLURONIC® and TECTONIC® polymers which are PEO-PPO (polyethyleneoxide-polypropyleneoxide) block copolymers, available from BASF Corporation, Chemicals Div., Wyandotte, Mich., USA; homopolymers and copolymers of acrylic acid e.g., CARBOPOL® polymers manufactured by BF Goodrich (Akron, Ohio); blends of polyoxyethylene or polyethylene glycols with polyacrylic acid such as POLYOX® polymers blended with CARBOPOL® polymers; polyacrylamides; cross-linked dextran such as SEPHADEX® (Pharmacia Fine Chemicals, AB, Uppsala, Sweden), WATER LOCK® (Grain Processing Corp., Muscatine, Iowa) which is a starch-graft-poly(sodium acrylate-co-acrylamide) polymer; cellulose polymers and derivatives thereof, such as methylcellulose, microcystalline cellulose, hydroxyethyl cellulose, hydroxypropylcellulose (e.g., KLUCEL® polymers), hydroxypropylmethylcellulose, low-substituted hydroxypropylcellulose, and cross-linked Na-carboxymethylcellulose such as Ac-Di-Sol (FMC Corp., Philadelphia, Pa.), carboxymethylcellulose (CMC), —SANGELOSE® (hydroxypropyl methylcellulose stearoxy ether) manufactured in Osaka, Japan, cationic celluloses, e.g., UCARE® POLYMER JR polymers, by Dow Personal Care; hydrogels, such as polyhydroxyethyl methacrylate (National Patent Development Corp.); polymethacrylates, e.g., EUDRAGIT®, ammonio methacrylate copolymer, methacrylic acid copolymer; gums/Polysaccharides and polysaccharide derivatives, such as sodium alginate, xanthan gum, gellan gum, welan gum, rhamsan gum, Carageenan, Ceratonia, Cross-linked high amylase starch, dextran, natural gums, chitosan, pectin, starch, guar gum, locust bean gum, and the like, as well as blends thereof; polyethyleneimines; maleic anhydrides; chitosan & derivatives; polyurethane hydrogels, poly (2-ethyl-2-oxazoline), etc.

The donor reservoir of the iontophoretic device may include additives chosen from those that are well known and conventional in the iontophoresis art. Such additives include, for example, humectants, emollients, anti-fungal agents, antimicrobial agents, preservatives, antioxidants, permeation enhancers (e.g., fatty acids, fatty acid esters, surfactants, semipolar solvents, alcohols, glycols, glycerides, sulfoxides, ulfoxides and similar compounds, oxazolidinones, terpenes, terpenoids, essential oils, urea, sunscreens and their derivatives, glycerol or propylene glycol esters, lactic acid and its esters), buffers, emulsifiers, suspending agents, lubricants, crosslinking agents, inclusion complexing agents, chelating agents, pH modifiers, flow aids, stabilizers, gelling agents, thickeners, protective colloids, and any combination thereof. Permeation enhancers that may be included in the donor reservoir include, but are not limited to, lauric acid, linoleic acid, menthone, cineole, pulegone, azone, oleic acid, terpineol, propylene glycol, butanediols, laurocapram, dimethyl acetamide, ethyl acetate, isopropyl myristate, laureth-3-oxyethylene ether, lauryl lactate, oleyl oleate, isopropyl myristate, isopropyl palmitate, glyceryl monooleate, glyceryl monostearate, glyceryl palmitostearate, butylene glycol, DMSO, oleyl alcohol, and any combinations thereof.

The subject iontophoretic devices may include a donor reservoir having a volume ranging from 0.05 to 50 ml. In certain aspects, the donor reservoir has a volume ranging from 0.1 to 10 ml, e.g., from 0.25 to 5 ml.

Counter Reservoirs

Electrophoretic devices of the present disclosure also include a counter reservoir which contains one or more electrolytes and permits electrical communication with a counter electrode (e.g., a cathode). Such electrical communication requires that electrons of the electrode be exchanged with ions in the counter (or "electrolyte") reservoir upon the application of electrical current. In certain embodiments, the electrical communication is not impeded to any excessive degree by intervening material(s) used in the construction of the iontophoretic device. Accordingly, the counter reservoir may be configured such that the resistivity of the interface between the electrode and the electrolyte reservoir is low.

The counter reservoir may include at least one electrolyte, e.g., an ionic or ionizable component that can act to conduct current toward or away from the electrode. Typically, the electrolyte comprises one or more mobile ions, the selection of which is dependent upon the desired application. Examples of suitable electrolytes include aqueous solutions of salts. According to one embodiment, the counter reservoir comprises an aqueous solution of salts, such as sodium chloride, potassium chloride, etc., having a concentration of less than 1 mole/liter (<1 M), e.g., at about physiological concentration. Other suitable electrolytes include salts of physiological ions including, but not limited to, potassium ($K^+$), chloride ($Cl^-$), and phosphate ($PO_4^{3-}$). The salt and its concentration can be selected as desired for the particular application.

In other aspects, the counter reservoir may comprise a material that is itself relatively immobile in the absence of an electric field, but that acts to deliver mobile ions in the presence of an electric field. In the latter case, the electrolyte can more properly be termed an "ion source". Examples of ion sources according to the invention include polyelectrolytes, ion exchange membranes and resins, non-ionic buffers that become ionic upon pH change, and other known ion sources.

The counter reservoir may include a matrix material adapted to absorb and hold a sufficient quantity of liquid (e.g., an aqueous NaCl solution) therein in order to permit ion transport therethrough by iontophoresis. In certain aspects, gauzes made of cotton or other absorbent fabrics as well as pads and sponges (both natural and synthetic) may be used. According to one embodiment, the donor reservoir includes a matrix composed, at least in part, of a hydrophilic polymer material (e.g., a hydrogel). Both natural and synthetic hydrophilic polymers may be used and are described elsewhere herein.

Additional chemical species may be selected for inclusion in the electrolyte reservoir. Such other species include any of the species described above with respect to the donor reservoir, and include without limitation, humectants, anti-fungal agents, chelation agents (e.g., citrate ions, EDTA), surfactants (e.g., non-ionic, cationic, or anionic), buffers, ionic excipients, osmolarity adjusters (e.g., polyethylene glycols, sugars), ionic antibiotics, penetration enhancers (e.g., alkanols), stabilizers, enzyme inhibitors, preservatives, thickening agents (e.g., acrylic acids, cellulose resins, clays, polyoxyethylenes), and any combination thereof.

Counter reservoirs included in the subject iontophoretic devices may have a volume ranging from 0.05 to 50 ml. In certain aspects, the donor reservoir has a volume ranging from 0.1 to 10 ml, e.g., from 0.25 to 5 ml.

Electrode Materials and Designs

Iontophoretic devices of the present disclosure include at least one donor electrode (and in some instances two or more donor electrodes) in electrical communication with the donor reservoir, and at least one counter electrode in electrical communication with the counter reservoir. In certain aspects, the donor electrode and/or counter electrode may be made of "inert" materials which remain unchanged during the passage of current. Examples include platinum, gold, and carbon. One potential drawback of using inert electrode materials is the possibility of pH changes at the electrode sites as a result of electrochemical oxidation of water at the anode (e.g., the donor electrode) and reduction of water at the cathode (e.g., the counter electrode). These reactions occur with current flow and produce acidic changes at the anode and alkaline changes at the cathode which can cause moderate or even severe skin irritation or burns with a skin-worn patch.

The pH changes which may result from the use of inert electrode materials can be eliminated by the use of "sacrificial" electrode materials, i.e., materials that are consumed by an electrochemical reaction during the passage of current. Accordingly, in certain embodiments of the present disclosure, the donor electrode(s) and/or counter electrode(s) are comprised at least in part of a sacrificial electrode material. For example, silver chloride (AgCl) in cathodes is reduced to silver during the passage of current. Conversely, sacrificial anodes are oxidized and may include materials such as silver, zinc, or other readily oxidizable metals (e.g., metals that oxidize in preference to water). In one aspect, the donor electrode is made of a material selected from Ag/AgCl and Zn/AgCl.

In iontophoretic devices of the present disclosure that employ sacrificial electrode materials, the sacrificial material content should at least be sufficient to deliver the intended amount of drug and to last for the intended delivery period. For example, the sacrificial donor and/or counter electrode may be designed to continue to function until the sacrificial material of the electrode is completely depleted, avoiding any premature break in electrical connection to the electrode during a prolonged delivery period.

Certain designs or constructions of sacrificial donor (e.g., anode) electrodes provide superior protection against premature failure, i.e., failure of the electrode due to a premature breach in the electrical connection (or "neck area" or "neck connecting segment") to the electrode before depletion of the sacrificial metal material in the electrode area. As used herein, the terms "neck area" or "neck connecting segment" of the donor electrode refer to the narrowest region of the electrode in contact with the donor medium (e.g., a hydrogel matrix containing a sphingosine-1-phosphate receptor agonist active agent). The neck area may be at an edge of the donor reservoir closest to the power source and provides electrical contact to the power source in the circuit. According to one embodiment of the present disclosure, the neck area of the donor electrode is made of a consumable material, e.g., a sacrificial material, having a width that is 5% or more, such as 10% or more, of the maximum donor electrode dimension (e.g., the maximum width in the case of a square or rectangular electrode, the diameter of a circular electrode, etc.), or as much as fully enveloping the electrode, the conductor arc is sufficient so that the electrode will be reliable in operation for the full prolonged delivery period calculated for depletion of sacrificial metal. Such electrode designs are described in International Publication No. WO 2010/027444, incorporated herein by reference in its entirety for all purposes.

In a related aspect, the electrode assembly of the iontophoretic device may include an accurate and positive shutoff or circuit breaking device incorporated into the donor electrode or associated circuit structure. For example, the iontophoretic device may include an electrode assembly configured such that an electrical connection between the donor electrode and the power supply (e.g., a "neck area", "neck connecting segment"), or any other portion of the circuit structure, is consumed when a designated dosage of a sphingosine-1-phosphate receptor agonist active agent has been iontophoretically delivered to the subject. In certain aspects, iontophoretic devices of the present disclosure may include an electrode assembly that includes a layered structure which has a base layer of conductive material which reacts (oxidizes or reduces) preferentially to the oxidation or reduction of water. Portions or sections of the base layer are coated with two upper layers which cover different portions of the base layer with a narrow strip of uncoated base layer remaining there between. The first upper layer contains the sacrificial or consumable material of the consumable electrode and is coated on the first portion or area of the base layer. The consumable material of the first upper layer is selected to be one which oxidizes or reduces in preference to the conductive material of the base layer so that during the operation of the circuit of the iontophoresis device, this material is consumed first. Part of the base layer is also covered by a second upper layer of non-conductive or insulating material coated on a second portion of the base layer, the second upper layer being spaced from the first upper layer to expose a narrow gap or linking area of exposed base layer material there between.

When electrical current flows through the circuit of an iontophoresis device incorporating the layered electrode assembly described above, consumption of the consumable materials will take place in a predetermined, ordered sequence. The first or consumable upper layer of consumable or sacrificial material is consumed first followed by the exposed narrow linking area of the base layer between the consumable material of the upper layer and the non-conducting or insulating material coated on the second portion of the base layer. Consumption of the much smaller narrow exposed linking area (which might be described as a "wear bar") of the base layer serves to sever the base layer, thereby breaking electrical circuit continuity in the base layer creating an open circuit condition and disabling the operation of the iontophoretic device. Electrophoretic devices incorporating layered electrode assemblies to provide accurate and positive shutoff or circuit breaking functionalities are described in U.S. Pat. No. 7,844,327, incorporated herein by reference in its entirety for all purposes.

In certain embodiments, iontophoretic devices of the present disclosure may include two or more donor electrodes (e.g., anodes) in the donor reservoir. Having multiple electrodes in the donor reservoir finds use, e.g., when the capability of iontophoretically delivering two or more dosages to a patient—optionally by activation of a switching device by the patient—is desirable. For example, iontophoretic devices of the present invention may include a counter reservoir containing a counter electrode (e.g., a cathode) and a donor reservoir containing a pair of donor electrodes (e.g., anodes) spaced and electrically isolated from each other, but electrically connected to respective conductors and to the material in the reservoir. A two-position switch element and a pair of power sources, which may be conventional button-type batteries or other suitable power sources) connected in series may be provided. Additional interconnecting conductor elements may be provided to achieve the desired connectivity. Using the switch, either donor electrode can be selectively connected or patched into a circuit which is completed by the application of the patch to the skin of a subject. Accordingly, each electrode permits the iontophoretic delivery of a corresponding dosage of active agent, which dosages may be readily controlled by the subject or health care provider by activation of a switch positioned, e.g., on an external surface of the device. Further details regarding iontophoretic devices that employ two or more donor electrodes, e.g., for delivery of multiple dosages of active agents can be found in U.S. Pat. No. 7,856,263, incorporated herein by reference in its entirety for all purposes.

Power Sources

Iontophoretic devices of the present disclosure include at least one power source electrically coupled to the donor reservoir and the counter reservoir to deliver a current to the skin via the donor reservoir/electrode. In one embodiment, the device is connected to a remote power source, such an electrical outlet, a microprocessor-controlled electrical instrument. In other embodiments, the power source is an electrochemical (e.g., electrolytic) power source, such as a lithium battery, a lithium ion battery, or an alkaline battery, which batteries are optionally replaceable, rechargeable and/or integrated into the iontophoretic device.

In still other embodiments, the power source is a galvanic power source. Galvanic power sources generally involve power supplied by a galvanic couple, including a pair of electrodes having amounts of dissimilar surface electroactive materials that inherently provide a voltage difference between the electrodes (e.g., an anode and cathode) and which typically are connected directly by a conductor. Accordingly, in certain aspects, iontophoretic devices of the present disclosure include a donor electrode made of a first electroactive material and a counter electrode made of a second electroactive material, wherein the first and second electroactive materials are different. As will be appreciated, iontophoretic devices of the invention may employ one or more power sources which are a combination of electrolytic and galvanic power sources.

The type of power source may be chosen according to factors relating to cost, particular use and convenience. In one aspect, the present invention provides a wearable, disposable iontophoretic patch that comprises an electrolytic power source (e.g., a button-type battery or any other battery that can be incorporated into a wearable iontophoretic device), a galvanic power source, or a combination of electrolytic and galvanic power sources. Electrolytic and galvanic power sources that find use in the invention are described, e.g., in U.S. Pat. No. 6,653,014, incorporated herein by reference in its entirety for all purposes.

The rate of transdermal delivery of the sphingosine-1-phosphate receptor agonist active agent is, in some instances, directly proportional to the current provided by the power source. In yet other instances, the rate of transdermal delivery of the sphingosine-1-phosphate receptor agonist active agent is not proportional to the current provided by the power source. According to one embodiment, iontophoretic devices of the present invention include a power source configured to provide current in a range of from 0.005 to 50 mAmp. For example, the power source may be configured to provide current in a range of from 0.01 to 25 mAmp, such as from 0.02 to 10 mAmp, e.g., from 0.04 to 5 mAmp.

The subject iontophoretic devices may include a power source configured (e.g., having a capacity) to provide a therapeutically effective dose of the sphingosine-1-phosphate receptor agonist active agent to a subject. The level of current flow and application time may be reported in units of milliamp minutes (mAmp-min) and directly correlates to the amount of active agent delivered. According to one embodiment, the power source is configured to provide a dose of a sphingosine-1-phosphate receptor agonist active agent of from 0.025 to 720,000 mAmp-min, such as from 0.05 to 504,000 mAmp-min, e.g., a dose of from 0.15 to 360,000 mAmp-min, e.g., 0.3 mAmp-min to 216,000 mAmp-min.

Methods

Aspects of the invention include methods of iontophoretically delivering a therapeutically effective amount of a sphingosine-1-phosphate receptor agonist active agent to the subject. By "therapeutically effective amount" is meant a level in the plasma or other internal bodily tissue or fluid that provides for reduction, inhibition, or prevention of the symptoms or mechanisms underlying a condition to be treated, e.g., as reviewed below.

The subject methods include the delivery of any suitable sphingosine-1-phosphate receptor agonist active agent, such as any of the active agents described above in the section entitled "Sphingosine-1-Phosphate Receptor Agonist Active Agents." For example, the sphingosine-1-phosphate receptor agonist active agent may be a 2-amino-1,3-propanediol compound. In certain aspects, the sphingosine-1-phosphate receptor agonist active agent may be a fingolimod salt, e.g., fingolimod HCl.

It should be understood that the methods of the invention are not limited to any particular iontophoretic device. Any device that finds use in iontophoretically delivering an active agent to a subject may be employed so long as the active agent is iontophoretically delivered into or through the skin of a subject. For example, any of the iontophoretic devices described herein or incorporated herein by reference may be used to deliver the sphingosine-1-phosphate receptor agonist active agent to the subject.

In practicing the invention, iontophoretically delivering the sphingosine-1-phosphate receptor agonist active agent may include attaching an iontophoretic device to a skin surface (e.g., any convenient skin surface) of the subject. Skin surfaces of interest include, but are not limited to: arms, leg, torso, head, neck, etc. The surface area that is covered by the iontophoretic device is generally sufficient to provide for the desired amount of sphingosine-1-phosphate receptor agonist active agent administration, and in certain embodiments ranges from 0.5 $cm^2$ to 1000 $cm^2$.

A subject delivery method will, in certain embodiments, provide a therapeutic level of sphingosine-1-phosphate receptor agonist active agent. In some embodiments, the iontophoretic delivery will provide a therapeutic level of a sphingosine-1-phosphate receptor agonist active agent (e.g., Fingolimod HCl) over a desired period of time, e.g. over a period of time of from 0.5 hour to 1 week. In certain embodiments, iontophoretically delivering a therapeutically effective amount of a sphingosine-1-phosphate receptor agonist active agent will provide a therapeutic level of a sphingosine-1-phosphate receptor agonist active agent over an extended period of time, where the therapeutic level of the sphingosine-1-phosphate receptor agonist active agent remains relatively constant in the individual over the extended period of time. A "relatively constant" level is a level that varies by 30% or less, e.g., 25% or less, including 20% or less, such as 15%, including 10%, e.g., 5% or less over a given period of time. By extended period of time is meant a time of 3 hr or longer, such as 2 days or longer, e.g., a time ranging from 0.5 days to 2 weeks, such as from 1 day to 1 week.

Parenteral administration of Fingolimod HCl for the treatment of multiple sclerosis is associated with adverse events (AEs) such as fatal viral infections, skin cancer, and macular edema in subjects to which Fingolimod HCl was orally administered. Iontophoretic delivery of sphingosine-1-phosphate receptor agonist active agents according to the subject methods provide more accurate control over the rate at which the sphingosine-1-phosphate receptor agonist active agent is administered to the subject. Moreover, the subject methods provide more constant systemic levels of the active agent during the administration period, thereby avoiding the substantial peak to trough fluctuations (as much as 45% for the phosphorylated (active) form of fingolimod and 20% for non-phosphorylated fingolimod) that have been observed with orally administered fingolimod HCl and which may underlie the AEs associated with this route of administration.

Accordingly, in certain aspects, the iontophoretic methods of the invention result in reduced incidence of adverse events (e.g., viral infections, skin cancer, and/or macular edema) as compared to parenteral (e.g., oral) routes of administration of the sphingosine-1-phosphate receptor agonist active agent (e.g., fingolimod HCl). For example, the subject methods may result in a reduced incidence of adverse events such as a 5%, 10%, 15%, 20%, 25%, 50%, 75% or more reduction in the incidence of adverse events as compared to orally administered sphingosine-1-phosphate receptor agonist active agent (e.g., fingolimod HCl).

In one aspect, the iontophoretic delivering comprises continuously delivering the sphingosine-1-phosphate receptor agonist active agent for a desired period of time, e.g., 1 hour longer, such as 6 hours or longer, including 12 hours or longer, e.g., one day or longer, using a single iontophoretic device. For example, an iontophoretic device may be attached to a skin surface of a subject and continuously deliver a desired amount of the sphingosine-1-phosphate receptor agonist active agent (e.g., fingolimod) for a prolonged amount of time, e.g., 1, 2, 3, 4, 5, 6, 7, or more days. The iontophoretic device for continuous and/or prolonged delivery may be a wearable and/or disposable iontophoretic device such as those described elsewhere herein.

According to certain embodiments, the subject methods include applying an iontophoretic device to a skin surface of the subject a single time or a plurality of times over a given time period, e.g., the course of the disease condition being treated, where the dosing schedule when a plurality of iontophoretic devices are employed over a given time period may be daily, weekly, biweekly, monthly, etc.

As reviewed in the Utility section below, methods and devices of the invention find use in the treatment of a variety of conditions, including immune system disorders, e.g., multiple sclerosis. In some embodiments, a subject delivery method treats an immune system disorder, e.g., the method is suitable for abortive therapy of an immune system disorder. In other embodiments, a subject delivery method prevents the occurrence of an immune system disorder. In some embodiments, a subject delivery method reduces or eliminates one or more symptoms of an immune system disorder. It will be understood that the immune system disorder may be any immune system disorder for which a sphingosine-1-phosphate receptor agonist active agent (e.g., fingolimod) is effective against, including autoimmune disorders, e.g., multiple sclerosis.

Individuals who are suitable for treatment with a subject delivery method include individuals suffering from an immune system disorder; and individuals who are prone to suffering from immune system disorders, e.g., individuals with a history of immune system disorders. Individuals who are suitable for treatment with a subject delivery method also include individuals suffering from relapsing remitting immune systems disorders, such as relapsing remitting multiple sclerosis. Individuals may be diagnosed as being in need of the subject methods using any convenient protocol, and are generally known to be in need of the subject methods prior to practicing the subject methods.

Generally, subjects suitable for treatment with a subject method are "mammals" or "mammalian." In certain embodiments, the subject will be a human.

Utility

The devices, methods, and kits of the invention are useful in numerous contexts, including the treatment of a variety of conditions. For example, the devices, methods, and kits find use in treating an immune system disorder in a subject. Immune systems disorders that may be treated according to the subject methods include, but are not limited to, multiple sclerosis, autoimmune encephalomyelitis, arthritis, lupus (e.g., lupus nephritis), transplant (e.g., allograft) rejection, and the like.

As set forth above, the sphingosine-1-phosphate receptor agonist active agent may be Fingolimod HCl. It has been shown that Fingolimod HCl is effective in treating a number of autoimmune disorders including multiple sclerosis. See, e.g., Kappos et al., Oral Fingolimod (FTY720) for Relapsing Multiple Sclerosis (2006) *N. Engl. J. Med.;* 355:1124-1140, and Cohen et al., Oral Fingolimod or Intramuscular Interferon for Relapsing Multiple Sclerosis (2010) *N. Engl. J. Med.* 362:402-415. In certain aspects, the subject methods are methods of treating multiple sclerosis in a subject, the methods including iontophoretically delivering a therapeutically effective amount of Fingolimod HCl to the subject.

Specific applications in which methods and devices described herein may be employed include, but are not limited to: those described in U.S. Pat. Nos. 5,604,229; 5,505,715; 6,004,565 and 6,121,329, as well as Published United States Patent Application Nos. 2005/0090520; 2009/0275553; 2010/0160259; and 2010/0168078.

Packaged Iontophoretic Systems

The present disclosure also provides packaged iontophoretic systems. The packaged systems include a package material that hermetically packages an iontophoretic system which, when assembled, is configured to transdermally deliver a sphingosine-1-phosphate receptor agonist active agent to a subject by iontophoresis. Package materials that find use in the subject iontophoretic systems may comprise water-impermeable materials selected from aluminum foil (e.g., a medical foil storage pouch), a polyester film, a polypropylene film, and a polyethylene film.

According to one embodiment, the iontophoretic system is a pre-assembled, self-contained, storage-stable iontophoretic device. For example, a donor reservoir and a counter reservoir of a packaged iontophoretic device may be "pre-loaded" with solution (optionally in a matrix such as a hydrogel) containing the sphingosine-1-phosphate receptor agonist active agent and a counter ion solution, respectively. Such pre-assembled iontophoretic systems are advantageous in that the need for users to incorporate the aqueous active agent reservoir or ion reservoir at the time of use is avoided.

In other embodiments, the present disclosure provides packaged iontophoretic systems for pre-use assembly. Exemplary packaged iontophoretic systems for pre-use assembly are described, e.g., in U.S. Pat. No. 6,745,071 and International Publication No. WO 2010/027468, the full disclosures of which are incorporated herein by reference in their entireties for all purposes. Packaged iontophoretic systems for pre-use assembly are advantageous in situations where "pre-loading" the iontophoretic device with active agent solution and ion solution would reduce the storage stability (or "shelf life") of the iontophoretic system due to factors such as the active agent being relatively unstable in solution and/or corrosion of metallic components and degradation of power sources resulting from exposure to the active agent and counter ion solutions during storage.

In one aspect, the subject packaged iontophoretic systems are for pre-use assembly and include a donor electrode and a shaped recess associated with the donor electrode, a donor matrix comprising a sphingosine-1-phosphate receptor agonist active agent and having a shape complementary to the recess associated with the donor electrode, a counter electrode and a shaped recess associated with the counter electrode, and a counter matrix having a shape complementary to the recess associated with the counter matrix. According to this aspect, the donor electrode, donor matrix, counter electrode, and counter matrix are arranged such that the iontophoretic system is assembled prior to use by folding the system such that the donor matrix and counter matrix are brought into conductive relation with the donor electrode and the counter electrode, respectively. Example of iontophoretic systems which are assembled prior to use by folding include those described in U.S. Pat. No. 6,745,071 and International Publication No. WO 2010/027468, the full disclosures of which are incorporated herein by reference in their entireties for all purposes.

The subject packaged iontophoretic systems which are for pre-use assembly by folding may be provided as a wearable (and optionally disposable) iontophoretic device that is prepackaged as a complete self-contained unit which includes the sphingosine-1-phosphate receptor agonist active agent to be administered and counter ions. The system includes a provision for isolating moisture sources from the electrodes and from the power source during storage to optimize shelf stability. The systems provide a simple, user-friendly mechanism to transfer the drug to be administered and counter ion reservoirs to the electrodes in order to activate the device circuit. The self-contained iontophoretic drug delivery systems permit the storage of all elements of the device in a single device to be activated in a single outer package. The sphingosine-1-phosphate receptor agonist active agent to be administered, as well as the particular ion species, may be selectively or optionally stored in either a dry state or a wet state in order to optimize shelf stability. Assembly of the iontophoretic system may include breaching the outer package material to reveal a substrate (or two or more operably connected substrates) that includes the donor electrode, the counter electrode, the donor matrix and the counter matrix, where the donor and counter matrices are isolated from the iontophoretic device via separation by water-impermeable membranes. To activate the device, the water impermeable membrane covers which isolate the donor and counter matrices may be peeled away and removed. The substrate is then folded inward on itself at predetermined locations to engage the donor and counter matrices with the donor and counter electrodes, respectively. One or more readily visible fold lines may be provided on the substrate to facilitate proper alignment as the device is folded.

Additional packaged iontophoretic systems for pre-use assembly are provided by the present disclosure. According to one embodiment, the subject packaged iontophoretic systems for pre-use assembly include a drug pack component comprising one or more matrices, and an iontophoresis patch component, wherein the iontophoresis patch component is configured to align with one or more matrices of the drug pack component in conductive relation in an assembled state. Optionally, the iontophoresis patch component includes a donor electrode and a counter electrode, where the iontophoresis patch component includes shaped recesses associated with the donor and counter electrodes, which recesses are configured to receive a matrix from the drug pack component. As will be appreciated, the drug pack component may contain one or more matrices (e.g., hydrogel-containing "pads") that include the sphingosine-1-phosphate receptor agonist active agent to be aligned with the donor electrode, as well as one or more matrices that include a counter ion solution to be aligned with the counter electrode. When the system includes a recess associated with the donor electrode, the recess is optionally configured to receive a donor matrix that comprises a sphingosine-1-phosphate receptor agonist active agent. The sphingosine-1-phosphate receptor agonist active agent may be a 2-amino-1,3-propanediol compound, such as a fingolimod salt (e.g., fingolimod HCl).

The matrices of the drug pack may be aqueous matrices, such as hydrogel pads having the sphingosine-1-phosphate receptor agonist active agent or counter ions incorporated therein. When the drug pack matrices are hydrogel drug pads, the pads optionally include agarose (e.g., 1-3% agarose), cross-linked polyvinyl alcohol (e.g., 10-12%), or other substances suitable for use in hydrogel compositions including, but not limited to, polyvinylpyrrolidone, methyl cellulose, hydroxypropyl methylcellulose and carboxymethyl cellulose. Fibrous materials, such as cellulose, polyester, or polypropylene may be incorporated into the matrix to assist in providing and retaining a defined shape of the matrix, and to facilitate adhesion of the matrices to a skin surface of a subject.

Kits

Also provided are kits, where the subject kits include an iontophoretic device that includes a donor reservoir, a counter reservoir, and a power source configured to electrically couple the donor reservoir and the counter reservoir. The kit further includes a sphingosine-1-phosphate receptor agonist active agent.

According to one embodiment, the subject kits are provided with the sphingosine-1-phosphate receptor agonist active agent present in the donor reservoir. Alternatively, the iontophoretic device and the sphingosine-1-phosphate receptor agonist active agent are provided separately. The sphingosine-1-phosphate receptor agonist active agent may be a 2-amino-1,3-propanediol compound, such as a fingolimod salt, e.g., fingolimod HCl.

Kits may include the sphingosine-1-phosphate receptor agonist active agent in an amount suitable for a single application (e.g., a unit dose, or single dose) or multiple applications. In instances in which composition is present in a kit in an amount sufficient for more than one application, multiple packages, as described above, may be provided with each containing an amount of the sphingosine-1-phosphate receptor agonist active agent for a single application.

The various components of the kits may be present in separate containers, or some or all of them may be pre-combined. For example, in some instances, one or more components of the kit, are present in a sealed package, as a pouch, which may be sterile, e.g., a sterile foil pouch or envelope.

The subject kits may also include instructions for how to use the iontophoretic device to deliver the sphingosine-1-phosphate receptor agonist active agent. The instructions may include information about dosing schedules etc., and/or how to assemble the iontophoretic device (when the device requires assembly before use). In certain embodiments, the subject kits can include instructions on how to use the sphingosine-1-phosphate receptor agonist active agent to treat a particular disease condition, e.g., an immune system disorder such as multiple sclerosis. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

Methods of Making Iontophoretic Devices

The present disclosure also provides methods of making iontophoretic devices. According to one embodiment, the methods include disposing an electrical circuit assembly on a substrate (e.g., a flexible backing layer), the electrical circuit assembly comprising a donor electrode, a counter electrode, and a power source electrically coupled to the donor and counter electrodes. The methods further include disposing a donor reservoir over the donor electrode, disposing a counter reservoir over the counter electrode, and filling the donor reservoir with a donor medium that includes a sphingosine-1-phosphate receptor agonist active agent.

In certain aspects, the donor reservoir comprises an absorbent pad, such as a hydrogel drug pad in which a sphingosine-1-phosphate receptor agonist active agent is incorporated. Filling the donor reservoir optionally includes providing the donor reservoir with a hydrogel comprising the sphingosine-1-phosphate receptor agonist active agent. According to certain embodiments, the sphingosine-1-phosphate receptor agonist active agent is a 2-amino-1,3-propanediol compound or salt thereof, such as a fingolimod salt, e.g., fingolimod HCl.

The following examples are offered by way of illustration and not by way of limitation.

Examples

I. In Vitro Iontophoretic Delivery of Fingolimod HCl

A. Experimental Conditions

To demonstrate the feasibility of iontophoretic delivery of Fingolimod HCl, in vitro experiments were performed wherein Fingolimod HCl was delivered through the epidermis of cadaver skin. Conditions for these experiments are provided in Table 1.

TABLE 1

| | Delivery with different electrodes and different concentration of receptor solutions | Delivery as a function of drug concentration |
|---|---|---|
| Membrane | Cadaver skin, Epidermis (LGF, Rec'd Jan. 20, 2011 (Frozen Jan. 20, 2011), 10-10039; 92/W/F-Back) | Cadaver skin, Epidermis (LGF; Rec'd Jan. 20, 2011 (frozen January 2011, 10-11054; 83/W/F-Thigh) |
| Donor | 0.5% Fingolimod HCl solution (Anode: Ag or Zn) | 0.25, 0.5, 0.75, 1, 2% Fingolimod HCl solution (Anode: Ag) |
| Receptor | 0.9% NaCl or 0.09% NaCl (Cathode: AgCl) | 0.09% NaCl (Cathode: AgCl) |
| Current | 0.425 mA | 0.425 mA |
| Franz cell opening area | 1.77 cm2 | 1.77 cm2 |
| Duration | 8 hr | 48 hr |
| Sampling time | 1, 2, 4, 6, 8 hr | 1, 2, 4, 6, 8, 10, 24, 28, 48 h |
| Replicates | 3 | 3 |

B. Results and Discussion

1. Delivery with Different Electrodes and Different Concentration of Receptor Solutions Table 2 provides a summary of the delivery efficiency of Fingolimod HCl through cadaver skin by electrochemical cells and passive delivery when using different electrodes and different concentrations of sodium chloride solution.

TABLE 2

| | | Active + passive | | | |
|---|---|---|---|---|---|
| | | Maximum | | Passive | |
| Electrodes | Receptor solutions | Maximum delivery efficiency (ug/cm2/hr), 0.425 mA, 1.77 cm2 | SD (n = 3) | Maximum delivery efficiency (ug/cm2/hr), 1.77 cm2 | SD (n = 3) |
| Ag/AgCl | 0.9% NaCl | 5.0 | 1.6 | — | — |
| Zn/AgCl | 0.9% NaCl | 5.8 | 0.4 | — | — |
| Zn/AgCl | 0.09% NaCl | 16.8 | 3.8 | — | — |
| Passive | 0.9% NaCl | — | — | 0 | 0 |
| Passive | 0.09% NaCl | — | — | 0 | 0 |

FIGS. 1A and 1B provide graphical representations of in-vitro Fingolimod HCl delivery obtained from a 0.5% Fingolimod HCl solution. FIG. 1(A) shows the cumulative drug delivered, and FIG. 1 (B) shows drug delivery efficiency.

As can be seen from the above results, over an 8 h period no Fingolimod HCl delivery was detected from passive delivery. Iontophoresis improved the skin permeation of Fingolimod. In addition, drug delivery with Zn and Ag electrodes showed similar results. Using a lower concentration of sodium chloride (0.09% NaCl) than the expected normal saline in the receiving solution significantly increased the observed flux. It is believed that this observation results from the greater chance for Fingolimod $H^+$ ion to transport out of the gel versus chloride ion transporting into donor side. During the first 2 hr period, the delivery efficiency of fingolimod is low and not proportional to the current. Possible reasons for this observation are that fingolimod may significantly bind to either the stratum corneum or glassware to retard the appearance of drug into the receiving phase.

2. Delivery as a Function of Drug Concentration

Table 3 provides a summary of: (a) delivery efficiency of Fingolimod HCl through cadaver skin by electrochemical cells; and (b) passive delivery when using different drug concentrations for 48 hr.

TABLE 3

| | Active + passive | | | |
|---|---|---|---|---|
| | Average | | Passive | |
| Donor/Concentration of fingolimod HCl solution | delivery efficiency (ug/cm2/hr), 0.425 mA, 1.77 cm2 | SD (n = 3) | Average delivery efficiency (ug/cm2/hr), 1.77 cm2 | SD (n = 3) |
| 0.25% | 4.8 | 0.7 | 0.8 | 0.6 |
| 0.50% | 5.0 | 0.6 | 0.9 | 0.7 |
| 0.75% | 4.5 | 0.6 | 0.8 | 0.7 |
| 1% | 4.5 | 0.6 | 0.7 | 0.6 |
| 2% | 4.2 | 0.7 | 1.4 | 1.2 |

Figure 2B:
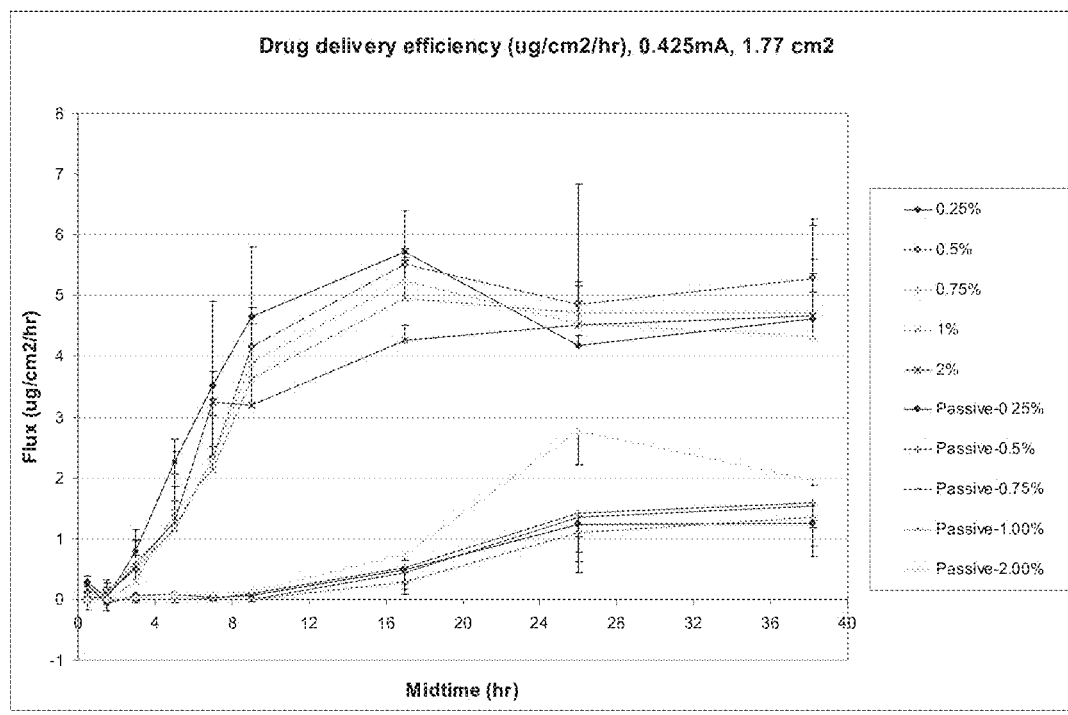

FIGS. 2(A) and 2(B) provide graphical results of in-vitro Fingolimod HCl delivery obtained from 0.25, 0.5, 0.75, 1 and 2% fingolimod HCl solutions. FIG. 2(A) shows the cumulative drug delivered, while FIG. 2(B) shows the drug delivery efficiency. FIG. 3 provides graphical results of in-vitro fingolimod HCl delivery as a function of drug concentration.

The above experiments provide the results of delivery of fingolimod as a function of concentration and show that iontophoretic delivery was maintained up to 48 hr. Passive delivery under the same experimental conditions was also concurrently investigated with the iontophoretic delivery and employed as a control. It was observed that 0.25, 0.5, 0.75, 1 and 2% fingolimod HCl solutions demonstrated similar delivery efficiency of about 4.5 µg/cm2/hr (active+passive) when the current applied was 0.425 mA and the area was 1.77 cm². The maximum efficiency could be reached at a concentration of less than 0.25%. After 8 hr., some passive delivery of fingolimod HCl through the skin was also observed. This observation may have resulted from the imperfection of the skin and the experimental design. In this study, the presence of pores from the micro-sized damage of the epidermis during the preparation of the epidermal membrane and from the appendages (hair follicles, sweat ducts) might facilitate the contact between donor and receptor site and contribute to the passive delivery of fingolimod HCl solution into the receptor solution.

As the rate of delivery at the beginning of the experiment was not proportional to the applied current, fingolimod may significantly bind to the stratum corneum to retard the appearance of drug into the receiving phase. The lag time of fingolimod delivery through the skin passively could be excessively long. Therefore, iontophoresis offers benefits to shorten the lag time of transdermal delivery and control the delivery of fingolimod.

The present study demonstrates that iontophoretic delivery of fingolimod HCl markedly improves the transdermal delivery of fingolimod HCl. Administration of fingolimod HCl by iontophoretic delivery will provide advantages not found in current delivery approaches (e.g., oral administration or passive transdermal patches), such as the ability to precisely control the rate of fingolimod delivery to achieve an optimum balance between efficacy and safety.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An iontophoretic device comprising:

a donor reservoir comprising a sphingosine-1-phosphate receptor agonist active agent;

a counter reservoir; and a power source electrically coupled to the donor reservoir and the counter reservoir that provides a current flow of from 0.01 mA to 25 mA sufficient to deliver the sphingosine-1-phosphate receptor agonist active agent from the donor reservoir such that cumulative delivery of the sphingosine-1-phosphate receptor agonist active agent is 5 μg/$cm^2$ or less in the first 2 hours after contacting the iontophoretic device to a subject.

2. The iontophoretic device according to claim 1, wherein the sphingosine-1-phosphate receptor agonist is a 2-amino-1,3-propanediol compound.

3. The iontophoretic device according to claim 1, wherein the sphingosine-1-phosphate receptor agonist is a fingolimod salt.

4. The iontophoretic device according to claim 2, wherein the fingolimod salt is selected from the group consisting of: fingolimod HCl, fingolimod HBr, fingolimod maleate, fingolimod fumarate and combinations thereof.

5. The iontophoretic device according to claim 1, wherein the donor reservoir comprises a sphingosine-1-phosphate receptor agonist active agent present in a donor medium.

6. The iontophoretic device according to claim 4, wherein the concentration of the sphingosine-1-phosphate receptor agonist active agent in the donor medium ranges from 0.004 mg/ml to 400 mg/ml.

7. The iontophoretic device according to claim 4, wherein the donor medium comprises a hydrogel.

8. The iontophoretic device according to claim 4, wherein the donor medium comprises an additive selected from a humectant and an anti-fungal agent.

9. The iontophoretic device according to claim 1, wherein the power source is selected from the group consisting of an electrical outlet, an electrolytic power source, a galvanic power source, and a combination thereof.

10. The iontophoretic device according to claim 8, wherein the power source is an electrolytic power source.

11. The iontophoretic device according to claim 8, wherein the power source is a galvanic power source.

12. The iontophoretic device according to claim 1, wherein the donor reservoir comprises two donor electrodes.

13. The iontophoretic device according to claim 1, wherein the donor reservoir comprises a donor electrode electrically coupled to the power source via an electrical connection comprising a consumable material.

14. The iontophoretic device according to claim 12, wherein the electrical connection has a width that is 5% or more of a maximum width of the donor electrode.

15. The iontophoretic device according to claim 12, wherein the device is configured such that consumption of the electrical connection during operation disrupts electrical continuity between the donor electrode and the power source.

16. The iontophoretic device according to claim 1, wherein the device is disposable.

17. The iontophoretic device according to claim 15, wherein the device is configured to be worn on the skin of a subject.

* * * * *